US009738585B2

(12) United States Patent
Karime

(10) Patent No.: US 9,738,585 B2
(45) Date of Patent: Aug. 22, 2017

(54) METHODS FOR PREPARING ACETIC ACID VIA ETHANE OXIDATION

(71) Applicant: SAUDI BASIC INDUSTRIES CORPORATION, Riyadh (SA)

(72) Inventor: Mustapha N. Karime, Riyadh (SA)

(73) Assignee: SAUDI BASIC INDUSTRIES CORPORATION, Riyadh (SA)

(*) Notice: Subject to any disclaimer, the term of this patent is extended or adjusted under 35 U.S.C. 154(b) by 0 days.

(21) Appl. No.: 14/787,661

(22) PCT Filed: May 13, 2014

(86) PCT No.: PCT/US2014/037886
§ 371 (c)(1),
(2) Date: Oct. 28, 2015

(87) PCT Pub. No.: WO2014/186386
PCT Pub. Date: Nov. 20, 2014

(65) Prior Publication Data
US 2016/0075629 A1 Mar. 17, 2016

Related U.S. Application Data

(60) Provisional application No. 61/822,674, filed on May 13, 2013.

(51) Int. Cl.
*C07C 51/16* (2006.01)
*C07C 51/43* (2006.01)
*C07C 51/215* (2006.01)

(52) U.S. Cl.
CPC ............ *C07C 51/43* (2013.01); *C07C 51/215* (2013.01)

(58) Field of Classification Search
CPC ....... C07C 51/43; C07C 53/08; C07C 51/215; G05B 19/0426; G05B 19/056; G05B 19/4097; G05B 2219/13044; G05B 2219/13113; G05B 2219/35134; G05B 2219/42186; G06F 3/0482; G06F 3/04842; G06F 3/04847; Y02P 90/265
See application file for complete search history.

(56) References Cited

U.S. PATENT DOCUMENTS

| 4,278,503 A * | 7/1981 | Zeitlin .................... B01D 3/14 203/28 |
| 4,338,464 A | 7/1982 | Harper et al. |
| 2008/0087041 A1* | 4/2008 | Denton ................ F25J 3/0214 62/618 |
| 2009/0292139 A1 | 11/2009 | Brazdil et al. |

FOREIGN PATENT DOCUMENTS

| WO | WO99/13980 | * 3/1999 |
| WO | 2005018804 A1 | 3/2005 |

OTHER PUBLICATIONS

Lin et al. (A Highly Catalytic System for the Direct Oxidation of Lower Alkanes by Dioxygen in Aqueous Medium. A Formal Heterogeneous Analog of Alkane Monooxygenases, J. Am. Chem. Soc. 114, 7307-7308, 1992).*
Rahman et al. (Direct conversion of ethane to acetic acid over H-ZSM-5 using H2O2 in aqueous phase, Applied Catalyst A: General, 456, pp. 82-87, Feb. 26, 2013).*
Sulzer pp. 1-16, 2006.*
International Search Report for PCT/US2014/037886 mailed Aug. 28, 2014, 5 pages.
Kalam, Abul, et al., "Direct conversion of ehane to acetic acid over H-ZSM-5 using H2O2 in aqueous phase", Applied Catalysis A:General, 456, 82-87 (2013).
Written Opinion of the International Searching Authority for PCT/US2014/037886 mailed Aug. 28, 2015, 7 pages.

* cited by examiner

*Primary Examiner* — Yevegeny Valenrod
*Assistant Examiner* — Blaine G Doletski
(74) *Attorney, Agent, or Firm* — Cantor Colburn LLP

(57) ABSTRACT

The present disclosures and inventions relate to methods for the preparation of acetic acid via the oxidation of ethane, including the preparation of high purity acetic acid that comprises very low concentrations of formic acid impurity. More specifically, described herein are methods for producing acetic acid comprising: a. producing a crude acetic acid composition comprising formic acid from ethane via ethane oxidation; and then b. purifying the crude acetic acid composition by crystallization to remove formic acid to achieve a purified acetic acid composition; wherein the formic acid is present in the purified acetic acid composition in an amount less than 0.2% by weight, based on the total weight of the purified acetic acid composition.

27 Claims, 1 Drawing Sheet

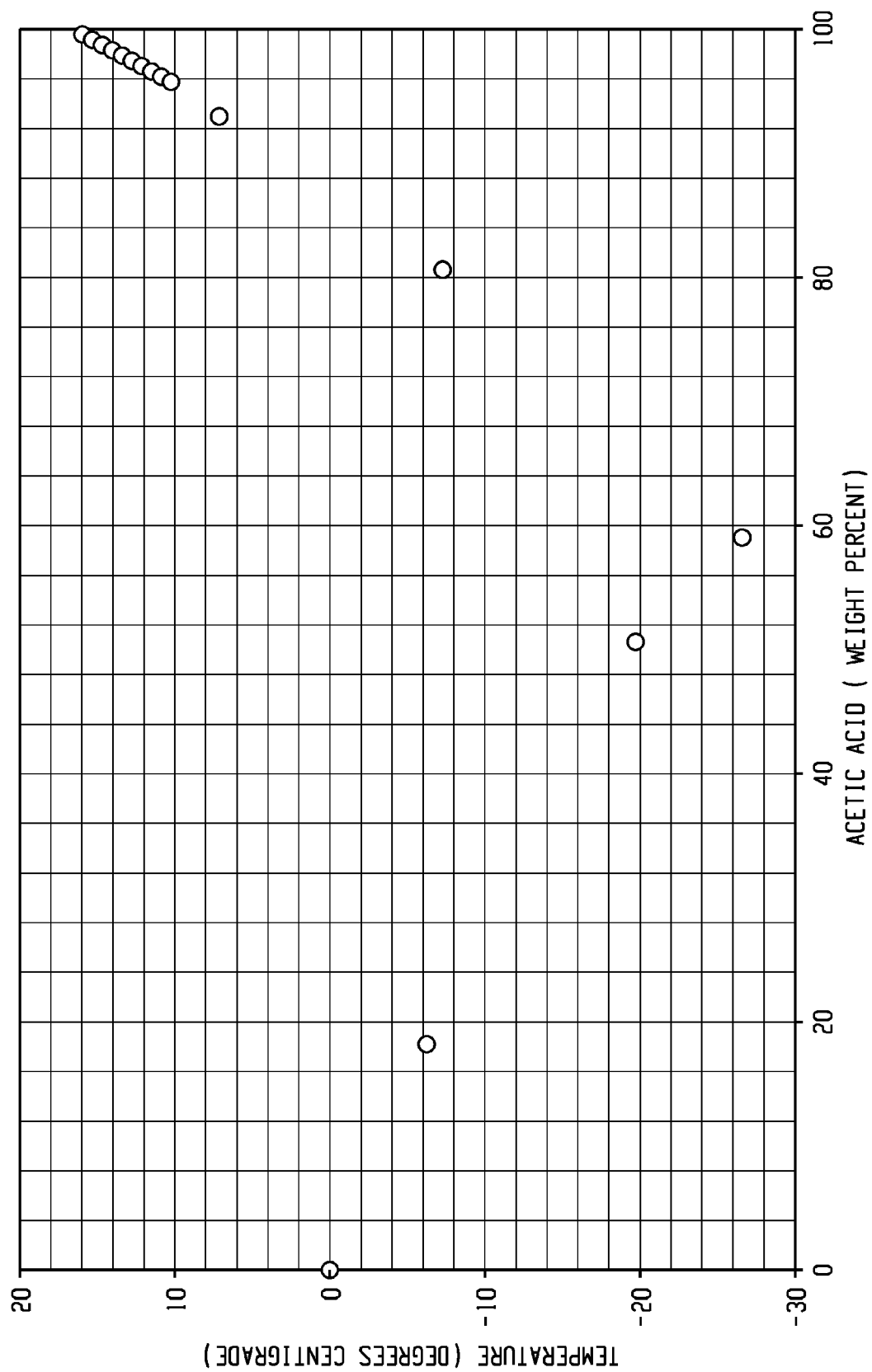

METHODS FOR PREPARING ACETIC ACID VIA ETHANE OXIDATION

CROSS-REFERENCE TO RELATED APPLICATION

This application is a national stage application of PCT/US2014/037886, filed May 13, 2014, which claims priority to U.S. Provisional Application Ser. No. 61/822,674 filed May 13, 2013, which are both hereby incorporated by reference in their entirety.

BACKGROUND

The present disclosure and invention relate to methods for the preparation of acetic acid via the oxidation of ethane, including the preparation of high purity acetic acid that comprises very low concentrations of formic acid impurity.

Ethane, $C_2H_6$, a colorless and odorless hydrocarbon gas at room temperature, is common in nature and can be isolated on an industrial scale during the purification of natural gas or as a byproduct of various petroleum refining processes, such as from catalytic cracking of higher hydrocarbons. The value and/or price of ethane is, however, currently relatively low, either as a fuel, or as a potential feedstock for making other petrochemicals such as ethylene, or acetic acid.

Acetic acid, $CH_3$—$CO_2H$, is a worldwide commodity produced at the level of hundreds of millions of tons per year, as a precursor for vinyl acetate monomer and polymers, and for making various acetate ester solvents and other chemicals. Although many processes for making acetic acid have been developed and commercially employed over the years, acetic acid production by methanol carboxylation is currently dominant in the chemicals industry. In those processes, methane or coal are converted to syngas (mixtures of hydrogen and carbon monoxide), then the syngas is catalytically converted to methanol, which is then reacted with carbon monoxide (separated from syngas) in the presence of rhodium or iridium iodide catalysts, to produce acetic acid. Although modern methanol carboxylation processes are quite efficient, they also require multiple steps and the use of high cost corrosion resistant materials of construction. Therefore, simpler and less capital intensive methods for making acetic acid remain of potential interest to industry, especially since efficient catalysts for hydrogenating acetic acid to make ethanol for use as an automotive fuel component have been discovered recently, so that the continuing expansion of the markets for acetic acid is expected in the long run.

While ethane oxidation processes produce fewer kinds and quantities of impurities heavier than ethanol, ethane oxidation processes also tend to produce relatively high quantities of formic acid, which because of its chemical and physical properties that are similar to acetic acid, is very difficult to separate from acetic acid, particularly to produce very high purity acetic acid containing very low levels of formic acid. Even low levels of formic acid in acetic acid are undesirable because the formic acid promotes corrosion of metal vessels used to make and store acetic acid.

Accordingly, there remains a need for new and less expensive methods for making high purity acetic acid. Applicants have developed such new methods, via application of the techniques of crystallization for purifying acetic acid made by the oxidation of ethane.

SUMMARY

In accordance with the purpose(s) of the invention, as embodied and broadly described herein, the present invention, in some aspects, satisfies these and other needs, by providing methods for purifying acids. In another aspect, methods for purifying acrylic acid and/or acetic acid are provided.

In some aspects, the invention is directed towards a method for producing acetic acid comprising: producing a crude acetic acid composition comprising formic acid from ethane via ethane oxidation; and then purifying the crude acetic acid composition by crystallization to remove formic acid to achieve a purified acetic acid composition; wherein the formic acid is present in the purified acetic acid composition in an amount less than 0.2% by weight, based on the total weight of the purified acetic acid composition.

The methods for producing acetic acid described and/or claimed herein have many aspects and variations, as will be obvious from the disclosures in this specification when read in combination with the knowledge of those of ordinary skill in the relevant arts. However, the specification disclosures and descriptions in the written description immediately below are not intended to be limiting on the claims attached hereto.

Additional advantages will be set forth in part in the description which follows, and in part will be obvious from the description, or can be learned by practice of the aspects described below. The advantages described below will be realized and attained by means of the chemical compositions, methods, and combinations thereof particularly pointed out in the appended claims. It is to be understood that both the foregoing general description and the following detailed description are exemplary and explanatory only and are not restrictive.

BRIEF DESCRIPTION OF THE FIGURES

The accompanying FIGURE, which is incorporated in and constitute a part of this specification, illustrate several aspects and together with the description serve to explain the principles of the invention.

The FIGURE shows a phase diagram for the crystallization of acetic acid/water mixtures over a range of acetic acid weight percentages and crystallization temperatures.

DETAILED DESCRIPTION

Disclosed herein are materials, compounds, compositions, and components that can be used for, can be used in conjunction with, can be used in preparation for the disclosed methods, or are products of the disclosed methods and compositions. It is to be understood that when combinations, subsets, interactions, groups, etc. of these steps, materials, and devices are disclosed that while specific reference of each various individual and collective combinations and permutation of these steps, materials, and devices cannot be explicitly disclosed, each is specifically contemplated and described herein. For example, if a catalyst component is disclosed and discussed, and a number of alternative solid state forms of that component are discussed, each and every combination and permutation of the catalyst component and the solid state forms that are possible are specifically contemplated unless specifically indicated to the contrary. This concept applies to all aspects of this disclosure including, but not limited to, steps in methods of making and using the disclosed compositions. Thus, if there are a variety of additional steps that can be performed it is understood that each of these additional steps can be performed with any specific aspect or combination of aspects of the disclosed methods, or in any order, and that each such combination or sequence is specifically contemplated and should be considered disclosed.

In this specification and in the claims which follow, reference will be made to a number of terms which shall be defined to have the following meanings:

It must be noted that, as used in the specification and the appended claims, the singular forms "a," "an" and "the" include plural referents unless the context clearly dictates otherwise. Thus, for example, reference to an acid includes mixtures of acids. "Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or cannot be substituted and that the description includes both unsubstituted lower alkyl and lower alkyl where there is substitution.

Ranges can be expressed herein as from "about" one particular value, and/or to "about" another particular value. As a default, when the term "about" is used in connection with a particular value, about can mean the value itself plus or minus about 10% of that particular value, unless another meaning is specified herein, or such a meaning is clearly inappropriate to one of ordinary skill in the art. When a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

The various aspects of the multiple methods for producing acetic acid described herein do however comprise at least two as shown above, and can also encompass additional steps, and/or limitations as further described in the written description below and dependent claims written below.

In many variations of the methods described, the ethane oxidation is performed in the gas phase from gaseous reactants (ethane and oxygen or air), and initially produces a mixture of reactor product steam vapors, which include some gaseous products (such as unreacted ethane and/or oxygen, ethylene, carbon monoxide, carbon dioxide) along with some reaction product vapors that can be readily condensed to liquid form (for example acetic acid, formic acid, and water). In contrast, the crude acetic acid composition is a liquid that comprises liquid acetic acid as a major component. Accordingly, the various processes described herein typically include one or more of a wide variety of possible steps intermediate between these steps to separate crude acetic acid in liquid form from the reactor product stream vapors. Accordingly, many aspects of the invention include an intermediate step of separating acetic acid from a reactor product steam produced by the ethane oxidation to form the crude acetic acid composition. In some aspects, the ethane oxidation utilizes $O_2$ and/or air as an oxidant.

The crude acetic acid composition is then purified by crystallization of acetic acid from the crude acetic acid composition, typically at low temperatures, to in order to remove water and/or organic impurities and to achieve the purified acetic acid composition. In many embodiments, the formic acid is present in the purified acetic acid composition in an amount less than about 0.2%, or less than about 0.1%, or less than about 0.05%, or less than about 0.03%, or less than about 0.01% by weight, based on the total weight of the purified acetic acid composition.

Described herein are methods for producing acetic acid comprising the steps of: producing a crude acetic acid composition comprising formic acid from ethane via ethane oxidation; and then purifying the crude acetic acid composition by crystallization to remove formic acid to achieve a purified acetic acid composition; wherein the formic acid is present in the purified acetic acid composition in an amount less than 0.2% by weight, based on the total weight of the purified acetic acid composition.

In some aspects, the method comprises producing a crude acetic acid composition comprising formic acid from ethane via ethane oxidation.

In another aspect, the method for producing acetic acid employs ethane (a gas at ambient temperature and pressure) as a very low cost starting material, which is readily available commercially from the purification of natural gas, or as a side product of many oil refining processes, such as steam cracking of higher hydrocarbons. In a further aspect, the ethane is extracted from natural gas.

The ethane oxidation step can be carried out in either gas or solution phases, and potentially can employ many potential oxidizing agents for oxidizing ethane such as oxygen gas (which can be alternatively termed diatomic oxygen, or $O_2$), hydrogen peroxide, inorganic peroxides, organic hydroperoxides, or ozone, or mixtures thereof. In another aspect, the oxidation is carried out in the gas phase using oxygen and/or air as an oxidant for ethane, optionally with the addition of one or more additional diluent/carrier gases (water/steam, nitrogen, $CO_2$, methane, and the like).

In some aspects, air is a frequent source for the oxygen gas used to oxidize ethane. In another aspect, air is used as an oxidant, and ethane can be present in an amount ranging from 1% vol to about 30% vol of ethane, based on the total volume of the crude acetic acid composition, is mixed with air in order to form a feed stream, including exemplary values of 3% vol, 5% vol, 7% vol, 9% vol, 10% vol, 12% vol, 14% vol, 16% vol, 18% vol, 20% vol, 22% vol, 24% vol, 26% vol, and 28% vol. In further aspects, the ethane can be present in an amount ranging from 10% vol to 20% vol based on the total volume of the crude acetic acid composition.

The ethane oxidation step can be carried out by combining ethane with oxygen and/or or air in the gas phase, then contacting the resulting ethane/oxygen gas mixture with a solid, liquid, or gaseous catalyst, in a reactor at atmospheric or higher pressures, and at elevated temperatures.

In such ethane oxidation reactions, ethylene ($CH_2$=$CH_2$, sometimes called "ethene") and acetic acid are two major reaction products in the reactions which are believed to occur according to the overall stoichiometry indicated below:

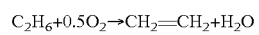

Smaller amounts of other oxygenated organic compounds can also be produced and be present in the reactor product stream vapors, such as carbon monoxide, carbon dioxide, and small amounts of formic acid, acetaldehyde (sometimes called ethanal), ethanol, and some small amounts of higher molecular weight organic oxygenated compounds. If ethane is used as feedstock, higher molecular weight organic oxygenated compounds are typically present at much lower concentrations than if heavier hydrocarbons (such as propane, butanes, pentanes, and hexanes) are used as a feedstock for oxidation.

In some aspects, the ethane oxidation utilizes a catalyst. A variety of catalysts can be employed to improve the rates and selectivity of the ethane oxidation for acetic acid production. A variety of known solid phase catalysts for the gas phase oxidation of ethane to mixtures of acetic acid are known and can be used in the processes described herein. European Patent Publications EP 02 94 845 (catalysts comprising $Mo_xV_yZ_z$ wherein z can be nothing or Nb, Sb, Ta, W etc.), EP 04 80 594 (metal oxide catalysts comprising tungsten, vanadium, rhenium, and an alkali metal), EP 04 07 091 (metal oxide catalysts comprising molybdenum, vanadium, rhenium, and an alkali metal), EP 05 18 548 (catalysts having the empirical formula $VP_aM_bO_x$ where M is one or more of Co, Cu, Re, Nb, W, and others), EP 06 27 401 (catalysts having the formula $V_aTi_bO_x$), and WO 99/13980 (metal oxide catalysts having the formula $Mo_aV_bNb_cX_d$ wherein X is selected from P, B, Hf, Te, and As) describe such catalysts for ethane oxidation, and appropriate combinations of temperature, pressure, mass flow in order to carry out the oxidation of ethane to mixtures of ethylene and acetic acid. Each of the references cited in this paragraph are hereby incorporated by reference for their teachings regarding formulas of the catalyst compositions described therein, their preparations, and conditions for their use in oxidizing ethane. In various aspects of the invention, the catalyst comprises a mixed Mo—V—Nb oxide, and can optionally comprise other metallic components.

The reaction product stream from the ethane oxidation can exit the reactor as a vapor stream (the reactor product stream), and can further comprise a mixture of unreacted ethane and/or oxygen, ethylene (ethene), acetic acid, water vapor, and nitrogen and/or any optional carrier/diluent gases, along with smaller amounts of gases of organic byproducts such as formic acid, ethanal (acetaldehyde), carbon monoxide, and $CO_2$, and possibly other heavier organic byproduct compounds in even smaller amounts.

This reactor product stream from the ethane oxidation, in the form of a mixed vapor, is not necessarily the crude acetic acid composition described in both steps of the method, which is a liquid steam. Accordingly, in various aspects of the invention, the ethane oxidation step producing the reactor product stream is further processed to an at least partially separate crude acetic acid to produce the liquid crude acetic acid composition, which is subjected to purification by crystallization as described.

At atmospheric pressure, the boiling point of acetic acid is 118-119° C., the boiling point of formic acid is 100.8° C., and the boiling point of water is 100° C., while the other major components of the reactor product stream (ethane, ethylene, oxygen, nitrogen, CO, $CO_2$, etc.) have lower boiling points, making them gases at such temperatures. As a result, in various aspects of the methods described herein, the reactor product stream vapors from ethane oxidation can be subjected to a cooling/condensation step, to at least partially condense acetic acid, water, and formic acid from the reactor product stream, so as to at least partially and/or substantially separate them from the gases the reactor product stream, such as ethane, oxygen, ethylene, carbon monoxide, carbon dioxide, or nitrogen, or other optional carrier/diluent gases.

This cooling/condensation step can be carried out at a pressure below the pressure in the oxidation reactor, but at or above atmospheric pressure, and at a temperature slightly below the boiling point of acetic acid at the pressure employed in the cooling/condensation step. For example, a cooling/condensation step can be carried out at atmospheric pressure or slightly above at a temperature between about 118-105° C., in order to at least somewhat selectively condense acetic acid from the reactor product stream vapors, to produce a liquid crude acetic acid composition that can be further purified as described herein. Such a liquid crude acetic acid composition can comprise a major portion of acetic acid. In some aspects, the crude acetic acid composition comprises water. In another aspect, the crude acetic acid composition further comprises acetaldehyde. In a further aspect, the crude acetic acid composition does not comprise butane, butene, propane, or propylene. In an even further aspect, the crude acetic acid composition does not comprise ethane, ethylene, butane, propane, propylene, or butene. The butane can be any isomer of butane including n-butane or iso-butane. The butene can be isomer of butene including 1-butene, Z-2-butene, E-2-butene, or iso-butene.

Additional optional process steps and/or methods can also be employed to further pre-purify the crude acetic acid composition before it is crystallized. For example, the crude acetic acid composition can optionally be further separated from formic acid, acetaldehyde, and water by a preliminary distillation (in either trayed or packed distillation columns) to produce a crude acetic acid composition comprising only small amounts of water or formic acid, then this pre-purified crude acetic acid composition can be subjected to crystallization. Accordingly, in some aspects the methods described herein further comprise the step of dehydrating the crude acetic acid composition, often by distillation, though other methods can be used. However, in some aspects of the methods described herein, the purification to remove formic acid and/or water does not comprise a distillation step. Similarly, in some aspects, the method further comprises one or more steps of dehydrating the crude acetic acid composition to produce a glacial acetic acid. In some aspects, the method further comprises the step of dehydrating the crude acetic acid composition to produce a glacial acetic acid. In another aspect, the method further comprises the step of dehydrating the crude acetic acid composition before the crystallization to remove formic acid.

In any event, the purity of the crude acetic acid composition produced in the ethane oxidation can vary considerably, though acetic acid can be the major component of the crude acetic acid compositions. In various aspects of the methods described herein, the acetic acid component is at least about 50 wt %, or at least about 60 wt %, or at least about 70 wt %, or at least about 80 wt %, or at least about 90 wt %, or at least about 95 wt %, or at least about 98 wt %, or at least about 99 wt % of the crude acetic acid composition by weight.

The crude acetic acid composition produced, and is then purified, by crystallization of acetic acid from the crude acetic acid composition at low temperatures, to substantially remove water and/or organic impurities, and to achieve/produce the purified acetic acid composition.

In a further aspect, the formic acid is present in the purified acetic acid composition in an amount less than about 0.2% by weight, based on the total weight of the purified acetic acid composition. In another aspect, the formic acid is present in the purified acetic acid composition in an amount ranging from 0.001% by weight to 0.2% by weight based on the total weight of the purified acetic acid composition, including exemplary values of 0.003% by weight, 0.005% by weight, 0.007% by weight, 0.01% by weight, 0.03% by weight, 0.05% by weight, 0.07% by weight, 0.09% by weight, 0.1% by weight, 0.13% by weight, 0.15% by weight, 0.17% by weight, and 0.19% by weight. In further aspects, the amount can be in a range derived from any two values. For example, the formic acid can be present in the purified acetic acid composition in an amount ranging from 0.003% by weight to 0.19% by weight based on the total weight of the purified acetic acid composition. In some aspects, the formic acid is present in the purified acetic acid composition in an amount less than 0.1% by weight based on the total weight of the purified acetic acid composition. In another aspect, the formic acid is present in the purified acetic acid composition in an amount less than 0.05% by weight based on the total weight of the purified acetic acid composition. In a further aspect, the formic acid is present in the purified acetic acid composition in an amount less than 0.03% by weight based on the total weight of the purified acetic acid composition. In an even further aspect, the formic acid is present in the purified acetic acid composition in an amount less than 0.01% by weight based on the total weight of the purified acetic acid composition.

Crystallization, also termed fractional crystallization, is a technique well known in the art of purifying organic compounds, both on lab and industrial scales. Technical information on fractional crystallization, including a technical brochure entitled "Fractional Crystallization" describing techniques for various methods of crystallization are available from Sulzer Chemtech of Winterthur Switzerland, a major supplier of industrial crystallization equipment, and are incorporated herein by reference for their description of the major technical factors, techniques, and equipment relevant to purifying organic materials by crystallization.

Crystallization of organic chemicals from solvents in general is well known, but not especially useful for purifying acetic acid, whose pure solid crystals melts to the pure liquid not far below room temperature, at the temperature of 16 to 17° C., and because crystallizing acetic acid from a solution would require very low temperatures. Melt crystallization, a technique of fractionally crystallizing organic materials by cooling a relatively pure liquid "melt" of the impure organic material, to form crystals of the material that are purer than the beginning "melt" is suitable for purifying acetic acid herein.

Various forms and techniques of fractional/melt crystallization can be suitable for purifying the crude acetic acid compositions produced by the methods described herein. All such forms of fractional crystallization comprise a step of substantially separating at least a portion of crystals comprising acetic acid from the surrounding liquid to form the purified acetic acid composition.

Static fractional crystallization involves cooling a static liquid melt of acetic acid, by cooling the walls of the vessel, causing crystals to grow on the walls of the vessel, then draining the remaining liquid to separate the remaining melt from the solid crystals, optionally followed by "sweating" the crystals (as further described below). A phase diagram for such static fractional crystallization separations of water and acetic acid are shown in FIG. 1. In some aspects of the methods described herein, the crystallization comprises a step of static fractional crystallization.

Falling film crystallization involves distributing a liquid melt of the crude acetic acid composition over a cooled surface, such as the surfaces of a tube, so that crystal formation occurs on the wall of the tube, optionally followed by "sweating" the crystals, then fully melting the crystals on the cooled surface walls to collect the purified acetic acid composition. In some aspects of the methods described herein, the crystallization comprises a step of falling film fractional crystallization.

The purity of the purified acetic acid composition produced by any of these fractional crystallization processes can typically be improved by "sweating" the solid acetic acid crystals initially formed and separated from their mother liquors. "Sweating" typically involves an additional step in the fractional crystallization process wherein the separated crystals comprising acetic acid are partially melted and substantially separated from the resulting melted liquid, then the remaining crystals are melted to form the purified acetic acid composition. Such "sweating" procedures improve the quality of the purified acetic acid, because it effectively washes away all the "mother liquor" from the original crystallization, which contains higher impurity levels than the crystals themselves, and also removes some of the outermost layers of the crystals themselves, which also tend to contain higher impurity levels than the inner portions of the original crystals.

The crystallization can be performed cooling liquids and forming suspensions of crystals within the liquids. Various methods for collecting such suspended crystals can be used, and can be conducted by various batchwise procedures, such as filtration, or by various continuous processes, such as for example those described by Gerard J. Arkenbout in CHEMTECH, vol. 6, September 1976, pages 596 to 599, which is hereby incorporated herein by reference for its teachings continuous techniques and/or equipment for continuous fractional crystallization processes. In such techniques, the crude acetic acid composition is subjected to one or more sequences of continuous fractional crystallization to remove water and/or formic acid, by the technique which cools the fraction to freeze out an acetic acid-water eutectic crystalline magma having an acetic acid content higher than the acetic acid content of said fraction, and leaves an acetic acid mother liquor having a water and/or formic acid content higher than the water and/or formic acid content of said fraction, and moves said crystalline magma countercurrent to the flow of the mother liquor, and melts at least a portion of the crystalline magma before its final composition is removed from the fractional crystallization system as product, and moves the melt liquor also countercurrent to the movement of the crystalline magma so that said flowing melt liquor and mother liquor wash the oppositely moving crystalline magma and mix to form a single waste liquor to be removed from the continuous crystallization system. In some aspects, the crystallization comprises continuous fractional crystallization.

One system can affect such cooling and countercurrent washing by chilling the liquid feed in a long horizontal crystallizer whose inner surfaces, cooled by indirect heat exchange, and are scraped by a helical screw end which advances the crystals as they begin to form near the feed end through to the discharge end. The resulting suspension of crystals in mother liquor discharges into the upper portion of a vertical column having a reciprocating piston periodically pushing down from the top of the column past the entry of the slurry into the column and forcing the slurry downward and then withdrawing toward the top of the column. The column also has, at the upper portion thereof a wall filter which extends from just below entry of the suspension down to slightly below the furthest downward thrust of the piston. The compression of the entering suspension by the piston forces mother liquor through the wall can filter and compact the crystals against the downwardly moving bed of previously compressed crystals. Near the bottom portion of the column a heating zone can be provided to melt the compacted crystals reaching said heating zone. A valved liquid product exit can be provided in the bottom of the column. The flow of liquid through the valve can be adjusted so that the downwardly moving bed of compacted crystals forces only a part of the melt of the crystals out of the bottom of the column which forces upwardly the remaining portion of the melt of the crystals. The upwardly forced portion of the melt of crystals can flow past the next upward adjacent portion of crystals before they move into the melting zone and can displace mother liquor from and/or melts the outer surfaces of the next upward adjacent portion of crystals, thus forming a new liquid in contact with them of lower impurity content which continues upward displacement of mother liquor from and/or melting outer layers of crystals contacted. As the bed of compressed crystals moves downward in contact with the upwardly moving liquid, new crystals form or crystals grow which can have a lower impurity content.

By the use of two or more of such continuous fractional crystallization systems in series flow relationship, the crude acetic acid composition can be processed to an anhydrous product comprising only extremely low levels of formic acid, as well as only extremely low levels of any heavy end impurities.

It is to be noted that the temperature required to crystallize acetic acid in such fractional crystallization processes depends on the purity of the crude acetic acid composition and/or its subsequently purified fractions. If the crude acetic acid composition is relatively impure (i.e. only about 50-70% acetic acid), the acetic acid can be crystallized at a temperature that ranges from about −35° C. to about −15° C. If the crude acetic acid composition is moderately impure, the acetic acid can be crystallized at a temperature that ranges from about −15° C. to about 17° C. If the crude acetic acid composition is relatively pure, i.e. above about 95% by weight, the acetic acid is crystallized at a temperature that ranges from about 10° C. to about 17° C.

Subsequent to one or more stages of fractional crystallization, the purified acetic acid composition comprises total impurities of an amount less than 2 wt %, based on the total weight of the purified acetic acid composition. In some aspects, the purified acetic acid composition comprises total impurities of an amount less than 1 wt %, based on the total weight of the purified acetic acid composition. In another aspect, the purified acetic acid composition comprises total impurities of an amount ranging from 0.001 wt % to 2 wt %, based on the total weight of the purified acetic acid composition, including exemplary values of 0.01 wt %, 0.015 wt %, 0.1 wt %, 0.15 wt %, 0.2 wt %, 0.3 wt %, 0.4 wt %, 0.5 wt %, 0.6 wt %, 0.7 wt %, 0.8 wt %, 0.9 wt %, 1 wt %, 1.2 wt %, 1.4 wt %, 1.6 wt %, and 1.8 wt %. In further aspects, the weight percentage can be in a range derived from any two exemplary values. For example, the purified acetic acid composition comprises total impurities of an amount ranging from 0.015 wt % to 1.8 wt % based on the total weight of the purified acetic acid composition.

In such purified acetic acid compositions, the impurities comprise water, ethane, ethene, ethanal, or formic acid, or combinations thereof.

The disclosed compositions and methods include at least the following aspects.

Aspect 1: A method for producing acetic acid comprising: producing a crude acetic acid composition comprising formic acid from ethane via ethane oxidation; and then purifying the crude acetic acid composition by crystallization to remove the formic acid to achieve a purified acetic acid composition; wherein the formic acid is present in the purified acetic acid composition in an amount less than 0.2% by weight, based on the total weight of the purified acetic acid composition.

Aspect 2: The method according to aspect 1, wherein the formic acid is present in the purified acetic acid composition in an amount less than 0.1% by weight, based on the total weight of the purified acetic acid composition.

Aspect 3: The method according to aspect 1, wherein the formic acid is present in the purified acetic acid composition in an amount less than 0.05% by weight, based on the total weight of the purified acetic acid composition.

Aspect 4: The method according to aspect 1, wherein the formic acid is present in the purified acetic acid composition in an amount less than 0.03% by weight, based on the total weight of the purified acetic acid composition.

Aspect 5: The method according to aspect 1, wherein the formic acid is present in the purified acetic acid composition in an amount less than 0.01% by weight, based on the total weight of the purified acetic acid composition.

Aspect 6: The method according to any of aspects 1-5, wherein the ethane is extracted from natural gas.

Aspect 7: The method according to any of aspects 1-6, wherein the ethane oxidation utilizes $O_2$ and/or air as an oxidant.

Aspect 8: The method according to any of aspects 1-7, wherein the ethane oxidation utilizes a catalyst.

Aspect 9: The method according to aspect 8, wherein the catalyst comprises a mixed Mo—V—Nb oxide.

Aspect 10: The method according to any of aspects 1-9, wherein the crude acetic acid composition does not comprise butane, butene, propane, or propylene.

Aspect 11: The method according to any of aspects 1-10, wherein the crude acetic acid composition further comprises acetaldehyde.

Aspect 12: The method according to any of aspects 1-11, wherein the crude acetic acid composition comprises water.

Aspect 13: The method according to any of aspects 1-12, wherein the crude acetic acid composition does not comprise ethane, ethylene, butane, propane, propylene, or butene.

Aspect 14: The method according to any of aspects 1-13, wherein the crystallization comprises static fractional crystallization.

Aspect 15: The method according to any of aspects 1-13, wherein the crystallization comprises falling film fractional crystallization.

Aspect 16: The method according to any of aspects 1-13, wherein the crystallization comprises continuous fractional crystallization.

Aspect 17: The method according to any of aspects 1-16, wherein the acetic acid is crystallized at a temperature that ranges from about −35° C. to about −15° C.

Aspect 18: The method according to any of aspects 1-16, wherein the acetic acid is crystallized at a temperature that ranges from about −15° C. to about 17° C.

Aspect 19: The method according to any of aspects 1-16, wherein the acetic acid is crystallized at a temperature that ranges from about 10° C. to about 17° C.

Aspect 20: The method according to any of aspects 1-19, wherein the crystallization comprises a step of substantially separating at least a portion of crystals comprising acetic acid from the surrounding liquid, to form the purified acetic acid composition.

Aspect 21: The method according to aspect 20, wherein the separated crystals comprising acetic acid are partially melted and substantially separated from the resulting melted liquid, and then the remaining crystals are melted to form the purified acetic acid composition.

Aspect 22: The method according to any of aspects 1-21, wherein the purification to remove formic acid does not comprise a distillation step.

Aspect 23: The method according to any of aspects 1-22, wherein the purified acetic acid composition comprises total impurities of an amount less than 2% by weight, based on the total weight of the purified acetic acid composition.

Aspect 24: The method according to any of aspects 1-22, wherein the purified acetic acid composition comprises total impurities of an amount less than 1% by weight, based on the total weight of the purified acetic acid composition.

Aspect 25: The method according to any of aspects 23-24, wherein the impurity comprises water, ethane, ethene, ethanal, or formic acid, or a combination thereof.

Aspect 26: The method according to any one of aspects 1-25, wherein the method further comprises the step of dehydrating the crude acetic acid composition.

Aspect 27: The method according to any one of aspects 1-26, wherein the method further comprises the step of dehydrating the crude acetic acid composition before the crystallization to remove formic acid.

Aspect 28: The method according to any one of aspects 1-27, wherein the method further comprises the step of dehydrating the crude acetic acid composition to produce a glacial acetic acid.

Aspect 29: The method according to any one of aspects 1-28, wherein the method further comprises an intermediate step of separating acetic acid from a reactor product stream produced by an ethane oxidation.

What is claimed is:

1. A method for producing acetic acid comprising:
   a. oxidizing ethane to produce a crude acetic acid composition comprising formic acid; and
   b. purifying the crude acetic acid composition by continuous fractional crystallization to remove the formic acid to produce a purified acetic acid composition;
   wherein the method further comprises the step of dehydrating the crude acetic acid composition before the crystallization to remove formic acid and wherein the formic acid is present in the purified acetic acid composition in an amount less than 0.2% by weight, based on the total weight of the purified acetic acid composition.

2. The method according to claim 1, wherein the formic acid is present in the purified acetic acid composition in an amount less than 0.1% by weight, based on the total weight of the purified acetic acid composition.

3. The method according to claim 1, wherein the formic acid is present in the purified acetic acid composition in an amount less than 0.05% by weight, based on the total weight of the purified acetic acid composition.

4. The method according to claim 1, wherein the formic acid is present in the purified acetic acid composition in an amount less than 0.03% by weight, based on the total weight of the purified acetic acid composition.

5. The method according to claim 1, wherein the formic acid is present in the purified acetic acid composition in an amount less than 0.01% by weight, based on the total weight of the purified acetic acid composition.

6. The method according to claim 1, wherein the ethane is extracted from natural gas.

7. The method according to claim 1, wherein the ethane oxidation utilizes $O_2$ and/or air as an oxidant.

8. The method according to claim 1, wherein the ethane oxidation utilizes a catalyst.

9. The method according to claim 8, wherein the catalyst comprises a mixed Mo—V—Nb oxide.

10. The method according to claim 1, wherein the crude acetic acid composition does not comprise butane, butene, propane, or propylene.

11. The method according to claim 1, wherein the crude acetic acid composition further comprises acetaldehyde.

12. The method according to claim 1, wherein the crude acetic acid composition comprises water.

13. The method according to claim 1, wherein the crude acetic acid composition does not comprise ethane, ethylene, butane, propane, propylene, or butene.

14. The method according to claim 1, wherein the crystallization comprises static fractional crystallization.

15. The method according to claim 1, wherein the crystallization comprises falling film fractional crystallization.

16. The method according to claim 1, wherein the acetic acid is crystallized at a temperature that ranges from about −35° C. to about −15° C.

17. The method according to claim 1, wherein the acetic acid is crystallized at a temperature that ranges from about −15° C. to about 17° C.

18. The method according to claim 1, wherein the acetic acid is crystallized at a temperature that ranges from about 10° C. to about 17° C.

19. The method according to claim 1, wherein the crystallization comprises a step of separating at least a portion of crystals comprising acetic acid from a surrounding liquid, to form the purified acetic acid composition.

20. The method according to claim 19, wherein the separated crystals comprising acetic acid are partially melted to form a resulting melted liquid and remaining crystals, separating the remaining crystals from the resulting melted liquid, and melting the remaining crystals to form the purified acetic acid composition.

21. The method according to claim 1, wherein the purification to remove formic acid does not comprise a distillation step.

22. The method according to claim 1, wherein the purified acetic acid composition comprises total impurities of an amount less than 2% by weight, based on the total weight of the purified acetic acid composition.

23. The method according to claim 1, wherein the purified acetic acid composition comprises total impurities of an amount less than 1% by weight, based on the total weight of the purified acetic acid composition.

24. The method according to claim 22, wherein the impurity comprises water, ethane, ethene, ethanal, or formic acid, or a combination thereof.

25. The method according to claim 1, wherein the method further comprises the step of dehydrating the crude acetic acid composition.

26. The method according to claim 1, wherein the method further comprises the step of dehydrating the crude acetic acid composition to produce a glacial acetic acid.

27. The method according to claim 1, wherein the method further comprises an intermediate step of separating acetic acid from a reactor product stream produced by an ethane oxidation.

* * * * *